United States Patent [19]

Stähle et al.

[11] 4,327,106
[45] Apr. 27, 1982

[54] 2-(PHENYL-AMINO)-2-IMIDAZOLINES AND SALTS

[75] Inventors: Helmut Stähle; Herbert Köppe; Werner Kummer, all of Ingelheim am Rhein, Fed. Rep. of Germany; Christian Lillie, Vienna, Austria

[73] Assignee: Boehringer Ingelheim GmbH, Ingelheim am Rhein, Fed. Rep. of Germany

[21] Appl. No.: 215,105

[22] Filed: Dec. 10, 1980

[30] Foreign Application Priority Data

Dec. 12, 1979 [DE] Fed. Rep. of Germany ....... 2950345

[51] Int. Cl.³ .................. A61K 31/415; C07D 231/06
[52] U.S. Cl. ................................ 424/273 R; 548/348; 548/351
[58] Field of Search .............................. 548/348, 351; 424/273 R

[56] References Cited

U.S. PATENT DOCUMENTS 3,773,767 11/1973 Stahle et al. ........................ 548/351

Primary Examiner—John M. Ford
Assistant Examiner—Robert C. Whittenbaugh
Attorney, Agent, or Firm—Hammond & Littell, Weissenberger & Muserlian

[57] ABSTRACT

Compounds of the formula

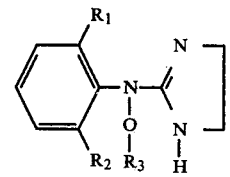

wherein $R_1$ and $R_2$, which may be identical to or different from each other, are each fluorine, chlorine, bromine or trifluoromethyl, and $R_3$ is alkyl of 1 to 4 carbon atoms, alkenyl of 2 to 4 carbon atoms, cyclopropylmethyl, benzyl or thienyl-2-methyl, and non-toxic, pharmacologically acceptable acid addition salts thereof. The compounds as well as their salts are useful as bradycardiacs.

8 Claims, No Drawings

2-(PHENYL-AMINO)-2-IMIDAZOLINES AND SALTS

This invention relates to novel 2-phenylamino-2-imidazolines and non-toxic acid addition salts thereof, to a method of preparing these compounds, to pharmaceutical compositions containing them as active ingredients, and to methods of using them as bradycardiacs.

More particularly, the present invention relates to a novel class of compounds represented by the formula

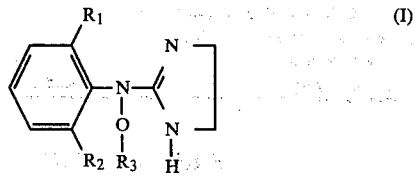

wherein $R_1$ and $R_2$, which may be identical to or different from each other, are each fluorine, chlorine, bromine or trifluoromethyl, and $R_3$ is alkyl of 1 to 4 carbon atoms, alkenyl of 2 to 4 carbon atoms, cyclopropylmethyl, benzyl or thienyl-2-methyl, and non-toxic, pharmacologically acceptable acid addition salts thereof.

The compounds embraced by formula I may be prepared by reacting a 2[(N-phenyl-N-hydroxy)-amino]-2-imidazoline of the formula

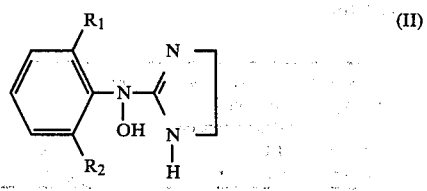

wherein $R_1$ and $R_2$ have the same meanings as in formula I, with a halide of the formula $$Hal-R_3 \quad (III)$$

wherein Hal is chlorine, bromine or iodine, and
$R_3$ has the same meanings as in formula I.

The reaction is preferably performed in the presence of a polar or non-polar solvent at room temperature, and the halide of the formula III is advantageously reacted with the sodium salt of the compound of the formula II.

The specific reaction conditions depend to a large extent upon the reactivity of the individual reactants. In general, it is recommended to provide the halide in excess and to perform the reaction in the presence of an acid-binding agent.

The starting compounds of the formula II are described in the literature (see German Offenlegungsschrift No. 2,457,979). The starting compounds of the formula III are obtained by halogenating the corresponding alcohols.

The compounds embraced by formula I are basic substances and therefore form addition salts with inorganic or organic acids. Examples of non-toxic, pharmacologically acceptable acid addition salts are those formed with hydrochloric acid, hydrobromic acid, hydroiodic acid, hydrofluoric acid, sulfuric acid, phosphoric acid, nitric acid, acetic acid, propionic acid, butyric acid, caproic acid, valeric acid, oxalic acid, malonic acid, succinic acid, maleic acid, fumaric acid, lactic acid, tartaric acid, citric acid, malic acid, benzoic acid, p-hydroxybenzoic acid, p-aminobenzoic acid, phthalic acid, cinnamic acid, salicylic acid, ascorbic acid, methane-sulfonic acid, 8-chlorotheophylline or the like.

The following examples illustrate the present invention and will enable others skilled in the art to understand it more completely. It should be understood, however, that the invention is not limited solely to the particular examples given below.

EXAMPLE 1

2-[N-Allyloxy-N-(2-bromo-6-fluoro-phenyl)-amino]-2-imidazoline 5.0 gm (0.016 mol) of 2-[N-(2-bromo-6-fluoro-phenyl)-N-hydroxy-amino]-2-imidazoline hydrochloride and 0.7 gm of sodium were dissolved in 75 cc of absolute ethanol, and then 1.6 ml (about 115% of the stoichiometrically required amount) of allyl bromide were added to the solution. The resulting mixture was stirred for one hour at room temperature, and was then evaporated. The residue was dissolved in dilute (about 1 N) hydrochloric acid, and the resulting solution was extracted with ether (the ethereal extracts were discarded). The acidic aqueous phase was then fractionally extracted with ether at stepwisely increasing pH-values (addition of 2-N-sodium hydroxide), and these ethereal extracts were also discarded. The aqueous phase was now made alkaline with 5 N sodium hydroxide, whereupon a white, amorphous substance precipitated, which was collected by suction filtration, washed with water and dried. 2.95 gm (58.3% of theory) of the compound of the formula

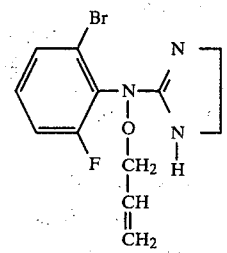

were obtained. It had a melting point of 141° C.

Using a procedure analogous to that described in Example 1, the compounds of the formula I shown in the following table were also prepared:

| Example No. | $R_1$ | $R_2$ | $R_3$ | Yield (% of theory) | Melting Point (°C.) |
|---|---|---|---|---|---|
| 2 | F | $CF_3$ | $-CH_2-CH=CH_2$ | 59.2 | 142 |
| 3 | Br | Br | $-CH_2-CH=CH_2$ | 62.2 | 167–168 |
| 4 | F | $CF_3$ | $-CH_2-\triangleleft$ | 7.9 | 117–119 |
| 5 | F | $CF_3$ | $-CH_2-CH=CH-CH_3$ | 45.3 | 110–111 |
| 6 | Br | F | $-CH_2-CH=CH-CH_3$ | 45.4 | 104 |
| 7 | Br | F | $-CH_2-CH_2-CH=CH_2$ | 18.0 | 105 |
| 8 | Br | Br | $-CH_2-CH=CH-CH_3$ | 52.8 | 121–122 |
| 9 | F | $CF_3$ | $-CH_2-\langle O \rangle$ | 60.4 | 113 |
| 10 | F | $CF_3$ | $-n-C_3H_7$ | 26.2 | 114 |
| 11 | F | $CF_3$ | $-CH_3$ | 44.5 | 119 |

-continued

| Example No. | R₁ | R₂ | R₃ | Yield (% of theory) | Melting Point (°C.) |
|---|---|---|---|---|---|
| 12 | F | CF₃ | —C₂H₅ | 48.0 | 137 |
| 13 | F | CF₃ | -n-C₄H₉ | 41.8 | 121 |
| 14 | F | F | —CH₂—CH=CH₂ | 40.0 | 127–128 |
| 15 | Cl | Cl | —CH₂— 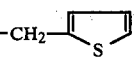 | 35.0 | 131–133 |
| 16 | Br | F | —CH₂— 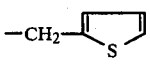 | 44.7 | 136–138 |
| 17 | F | CF₃ | —CH₂— 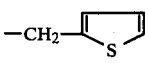 | 40.8 | 97–99 |
| 18 | Br | Br | —CH₂— 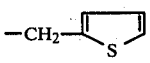 | 28.4 | 125–127 |

The compounds of the present invention, that is, those embraced by formula I above and their non-toxic, pharmacologically acceptable acid addition salts, have useful pharmacodynamic properties. More particularly, they exhibit bradycardiac activity in warm-blooded animals such as rats and rabbits.

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, emulsions, suspensions, syrups, suppositories and the like. One effective dosage unit of the compounds according to the present invention is from 0.0014 to 1.14 mgm/kg body weight, preferably 0.014 to 0.42 mgm/kg body weight.

The following examples illustrate a few pharmaceutical dosage unit compositions comprising a compound of the present invention as an active ingredient and represent the best modes contemplated of using the invention. The parts are parts by weight unless otherwise specified.

EXAMPLE 19

Coated tablets

The tablet core composition is compounded from the following ingredients:

| | | |
|---|---|---|
| 2-[N-Allyloxy-N-(2-bromo-6-fluoro-phenyl)-amino]-2-imidazoline | 5 | parts |
| Lactose | 65 | " |
| Corn starch | 130 | " |
| Sec. calcium phosphate | 40 | " |
| Soluble starch | 3 | " |
| Magnesium stearate | 3 | " |
| Colloidal silicic acid | 4 | " |
| Total | 250 | parts |

PREPARATION

The active ingredient is admixed with a portion of the excipients, the mixture is thoroughly kneaded with an aqueous solution of the soluble starch, and the moist mass is granulated by passing it through a screen. The granulate is dried, admixed with the remainder of the excipient, and the composition is compressed into 250 mgm-tablet cores which are subsequently coated with a thin shell consisting essentially of a mixture of sugar, talcum and gum arabic. Each coated tablet is an oral dosage unit composition containing 5 mgm of the active ingredient.

EXAMPLE 20

Hypodermic solution

The solution is compounded from the following ingredients:

| | |
|---|---|
| 2-[N-Allyloxy-N-(2-bromo-4-fluoro-phenyl)-amino]-2-imidazoline | 1.0 parts |
| Sodium chloride | 18.0 parts |
| Distilled water | q.s.ad 2000.0 parts by vol. |

PREPARATION

The active ingredient and the sodium chloride are dissolved in the distilled water, the solution is filtered until free from suspended particles, and the filtrate is filled into 2 cc-ampules in an atmosphere of nitrogen. The contents of each ampule are an injectable dosage unit composition containing 1 mgm of the active ingredient.

EXAMPLE 21

Drop solution

The solution is compounded from the following ingredients:

| | | |
|---|---|---|
| 2-[N-Allyloxy-N-(2-bromo-4-fluoro-phenyl)-amino]-2-imidazoline | 0.02 | parts |
| Methyl p-hydroxy-benzoate | 0.07 | parts |
| Propyl p-hydroxy-benzoate | 0.03 | parts |
| Demineralized water | q.s.ad 100 | parts by vol. |

PREPARATION

The active ingredient and the p-hydroxy-benzoates are dissolved in the demineralized water, the resulting solution is filtered, and the filtrate is filled into 100 ml-bottles equipped with a dropping spout 0.5 ml (about 20 drops) of the solution are an oral dosage unit composition containing 1 mgm of the active ingredient.

Any one of the other compounds embraced by formula I or a non-toxic, pharmacologically acceptable acid addition salt thereof may be substituted for the particular active ingredient in Examples 19 through 21. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

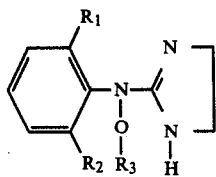

wherein
  $R_1$ and $R_2$ are each fluorine, chlorine, bromine or trifluoromethyl, and
  $R_3$ is alkyl of 1 to 4 carbon atoms, alkenyl of 2 to 4 carbon atoms, cyclopropylmethyl, benzyl or thienyl-2-methyl,
or a non-toxic, pharmacologically acceptable acid addition salt thereof.

2. A compound of claim 1, which is 2-[N-allyloxy-N-(2-bromo-6-fluoro-phenyl)-amino]-2-imidazoline or a non-toxic, pharmacologically acceptable acid addition salt thereof.

3. A compound of claim 1, which is 2-[N-allyloxy-N-(2-fluoro-6-trifluoromethyl-phenyl)-amino]-2-imidazoline or a non-toxic, pharmacologically acceptable acid addition salt thereof.

4. A compound of claim 1, which is 2-[N-n-propoxy-N-(2-fluoro-6-trifluoromethyl-phenyl)-amino]-2-imidazoline or a non-toxic, pharmacologically acceptable acid addition salt thereof.

5. A compound of claim 1 which is 2-[N-(cyclopropyl-methoxy)-N-(2-fluoro-6-trifluoromethyl-phenyl)-amino]-2-imidazoline or a non-toxic, pharmacologically acceptable acid addition salt thereof.

6. A compound of claim 1, which is 2-[N-benzyloxy-N-(2-fluoro-6-trifluoromethyl-phenyl)-amino]-2-imidazoline or a non-toxic, pharmacologically acceptable acid addition salt thereof.

7. A compound of claim 1, which is 2-[N-(thienyl-2-methoxy)-N-(2,6-dibromo-phenyl)-amino]-2-imidazoline or a non-toxic, pharmacologically acceptable acid addition salt thereof.

8. A bradycardiac pharmaceutical dosage unit composition consisting essentially of an inert pharmaceutical carrier and an effective bradycardiac amount of a compound of claim 1.

* * * * *